(12) United States Patent
Chen (10) Patent No.: US 8,783,115 B2
(45) Date of Patent: Jul. 22, 2014

(54) SYSTEM AND METHOD FOR MEASURING CABLE BENDING FORCE AND CABLE KINK FORCE

(75) Inventor: David Zhi Chen, Richardson, TX (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 65 days.

(21) Appl. No.: 13/492,977

(22) Filed: Jun. 11, 2012

(65) Prior Publication Data

US 2013/0327152 A1    Dec. 12, 2013

(51) Int. Cl.
*G01N 3/08*    (2006.01)

(52) U.S. Cl.
USPC ............................................................ 73/818

(58) Field of Classification Search
USPC ............................................................ 73/818
See application file for complete search history.

(56) References Cited

U.S. PATENT DOCUMENTS

| 5,038,622 A * | 8/1991 | Tijmann | 73/862.393 |
| 2002/0059834 A1 * | 5/2002 | Onoue | 73/812 |

* cited by examiner

*Primary Examiner* — Lisa Caputo
*Assistant Examiner* — Brandi N Hopkins (57) ABSTRACT

A test apparatus includes a first surface configured to apply a linear force in two directions and a first attachment assembly configured to secure a first end of a cable to the first surface. The first attachment assembly is further configured to permit two degrees of rotational freedom. The test apparatus also includes a second surface, opposite the first surface, and a second attachment assembly configured to secure a second end of the cable to the second surface. The apparatus facilitates testing of a bending force and a kink force associated with the cable.

20 Claims, 7 Drawing Sheets

SYSTEM AND METHOD FOR MEASURING CABLE BENDING FORCE AND CABLE KINK FORCE

BACKGROUND

Fiber optic cables are used for providing telecommunication services to business and residential locations. Some fiber optic cables are required to meet particular standards for outdoor installation. More particularly, for underground cable installation within a duct, both the cable and the duct must be tested by a certified independent test lab before being approved for use.

Blow-in cable technology (or cable jetting) is the process of blowing a cable through a duct while simultaneously pushing the cable into the duct. For effective blow-in installation of small diameter cables in a microduct, the installed cable must meet particular requirements. Cable that is too soft may jam in the conduit, while cable that is too stiff will not be able to bend around corners. Thus, cables must be tested to ensure a certain range of bending force and kink resistance for effective blow-in installation.

DETAILED DESCRIPTION OF PREFERRED EMBODIMENTS

The following detailed description refers to the accompanying drawings. The same reference numbers in different drawings may identify the same or similar elements.

Systems and methods described herein may provide for testing of cable bending force and cable kink force for small-diameter fibers (e.g., with diameters suitable for use with blow-in cable technology). The systems and methods allow for both compression and pull testing of a cable so that cable compression forces and kink limiting forces can be properly registered. Cables may be constrained within a test platform using an attachment assembly that provides two degrees of rotational freedom to prevent test curve discontinuities.

In one implementation, a test apparatus may include a first surface configured to apply a linear force in two directions (e.g., compression and tension) and a first attachment assembly configured to secure a first end of a cable to the first surface. The first attachment assembly may be further configured to permit two degrees of rotational freedom. The test apparatus may also include a second surface, opposite the first surface, and a second attachment assembly configured to secure a second end of the cable to the second surface. The apparatus may facilitate testing of a bending force and a kink force associated with the cable.

In another implementation, a method may include providing a cable test platform that includes two cable attachment assemblies. The cable attachment assemblies may be configured to provide two degrees of rotational freedom. The method may include securing ends of the cable to the cable attachment assemblies to form a loop between the ends of the cable, applying a tensile force to the cable via the cable attachment assemblies, and determining a kink force for the cable based on the applied tensile force. Additionally, the method may include securing ends of another cable to the cable attachment assemblies to form a straight run between the ends of the cable, applying a compressive force to the other cable via the cable attachment assemblies, and determining a bending force for the other cable based on the applied tensile force.

Figure 1A:
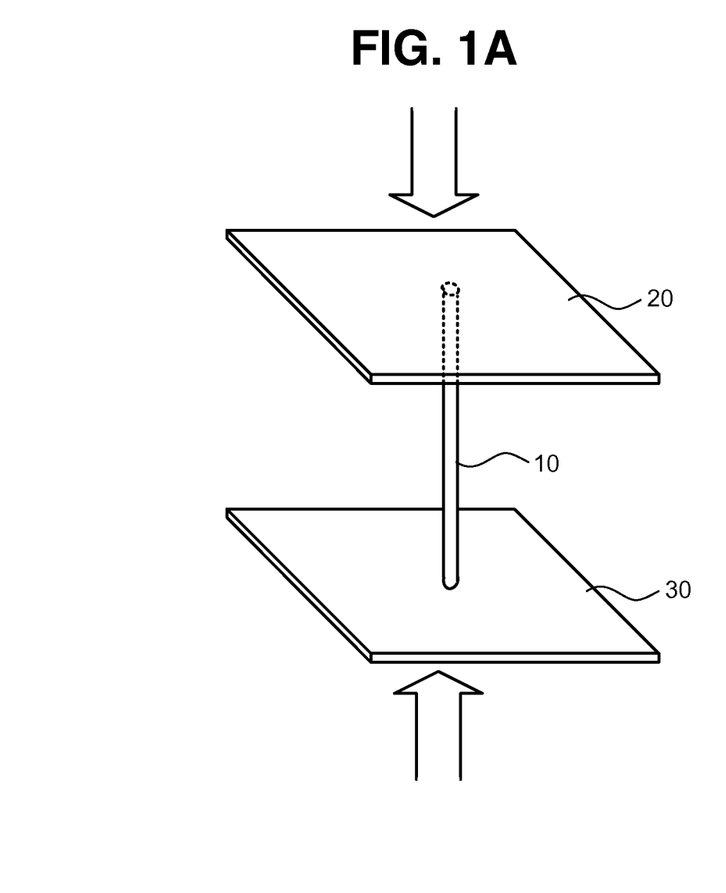
FIGS. 1A and 1B are diagrams illustrating concepts described herein.
Figure 1B:
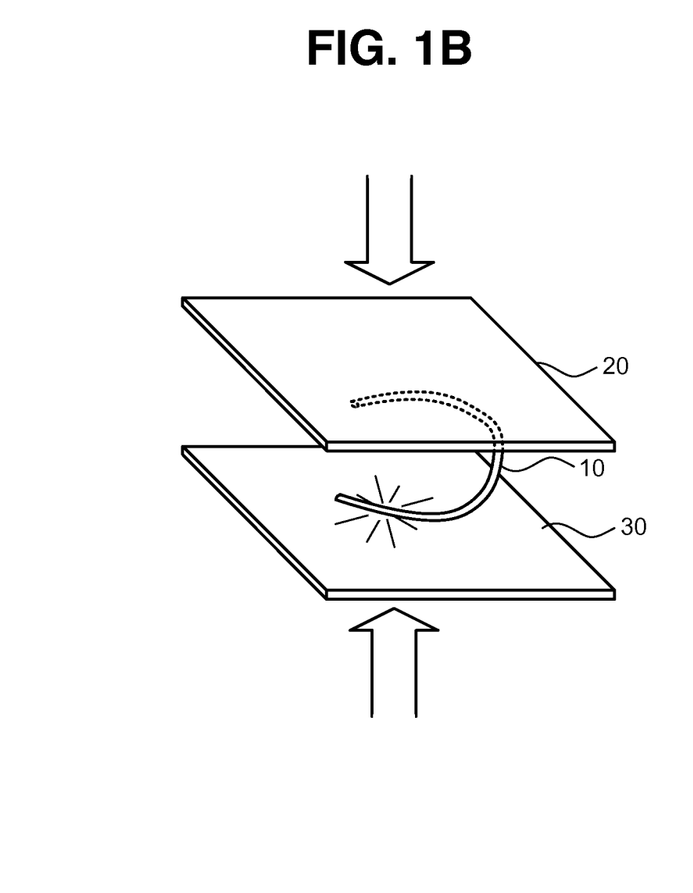

FIGS. 1A and 1B are diagrams illustrating concepts described herein. As shown in FIG. 1A, a cable 10 may undergo compression forces applied by, for example, flat plates 20 and 30. Flat plates 20 and 30 may be connected to, for example, hydraulic cylinders or other mechanisms that apply controlled linear forces (e.g., in the directions shown in FIG. 1A). In conventional test platforms, cable 10 may not be attached to either of flat plates 20 or 30. A rough (e.g., sandpaper-like) surface may be used on flat plates 20 and 30 to prevent slippage where the ends of cable 10 contact flat plates 20 and 30, respectively.

As flat plates 20 and 30 apply compressive forces and come together, cable 10 will bend. Eventually, as shown in FIG. 1B, the endpoints of cable 10 will lose contact with plates 20 and 30 in a conventional test platform. When the endpoints of cable 10 separate from plates 20 or 30, the forces from plates 20 and 30 may be applied at another location (e.g., closer to the middle) of cable 10. Because forces from plates 20 and 30 are applied at different points (e.g., not the endpoints) of cable 10, the effective bending cable length of cable 10 changes during the test. This change can cause a discontinuity in a test plot (e.g., graphing of applied force vs. distance between plates 20 and 30). Furthermore, when cable 10 is not attached to either of plates 20 or 30, conducting a kink test via a pulling motion of plates 20 and 30 is not feasible. Thus, in implementations provided herein, a test platform is provided that maintains contact between the endpoints of cable 10 and the sources of applied force.

Figure 2:
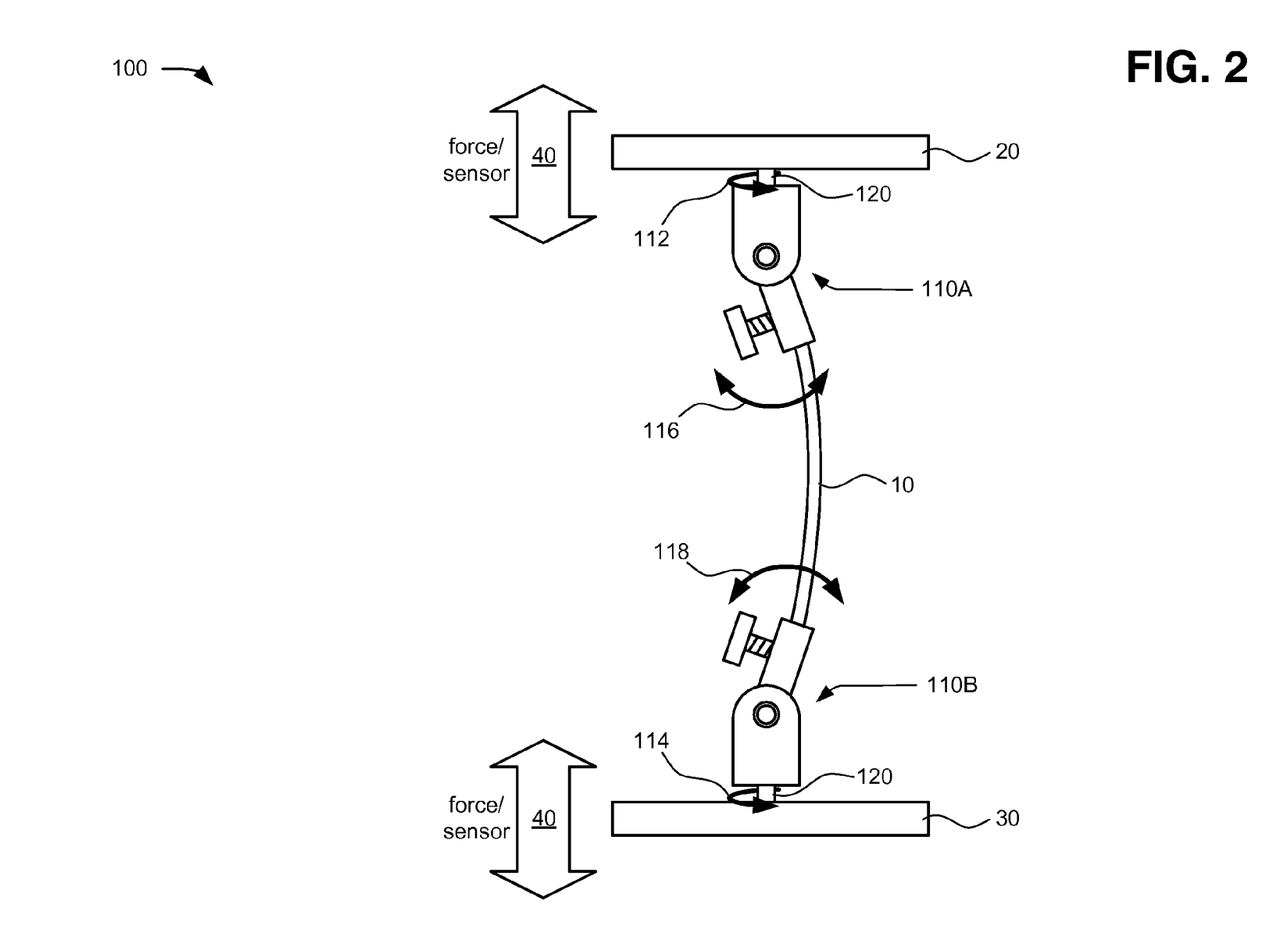
FIG. 2 is a diagram of an exemplary cable test platform according to an implementation described herein.

FIG. 2 is a diagram of an exemplary cable test platform 100 according to an implementation described herein. Cable test platform 100 may include plates 20 and 30 and a pair of attachment assemblies 110A and 110B (referred to herein collectively as "attachment assemblies 110" and generically as "attachment assembly 110"). One or both of plates 20 and 30 may be connected to a force/sensor mechanism 40 to selectively apply measured compressive or tensile forces to cable 10. For example, one or both of plates 20 and 30 may be connected to a hydraulic cylinder or another mechanism that can apply controlled forces in two directions. The hydraulic cylinders or other mechanisms may include, for example, sensors to measure applied forces.

Attachment assemblies 110 may secure ends of cable 10 to plates 20 and 30. More particularly, in the example of FIG. 2, one portion of attachment assembly 110A may be connected to plate 20 and another portion of attachment assembly 110A may be connected to one end of cable 10. Similarly, one portion of attachment assembly 110B may be connected to plate 30 and another portion of attachment assembly 110B may be connected to an opposite end of cable 10. In one implementation, attachment assemblies 110A and 110B may be identical, but for their installed orientation (e.g., facing up or down).

Consistent with embodiments described herein, each of attachment assemblies 110 may provide two degrees of freedom of rotation for an attached cable 10. The first degree of freedom may be represented as rotation within a plane generally parallel to the plane of plates 20/30. As shown in FIG. 2, each attachment assembly 110 may be connected by a fastener 120 to rotate in a plane parallel to plate 20/30, indicated by reference number 112 for attachment assembly 110A and reference number 114 for attachment assembly 110B. The second degree of freedom may be represented as rotation generally about an axis that is generally parallel to the plane of plates 20/30. As shown in FIG. 2, a portion of each attachment assembly 110 may rotate in the direction indicated by reference number 116 for attachment assembly 110A and by reference number 118 for attachment assembly 110B. Attachment assemblies 110 are described further in connection with FIGS. 3-4C.

Although FIG. 2 shows exemplary components of cable test platform 100, in other implementations, cable test platform 100 may include fewer, different, differently-arranged, or additional components than those depicted in FIG. 2. For example, in another implementation, cable test platform 100 may include only one attachment assembly 110 that has two degrees of rotational freedom. A differently-configured attachment assembly (e.g., with zero, one, or unlimited degrees of rotational freedom) may be used to secure the opposite end of the tested cable.

Figure 3:
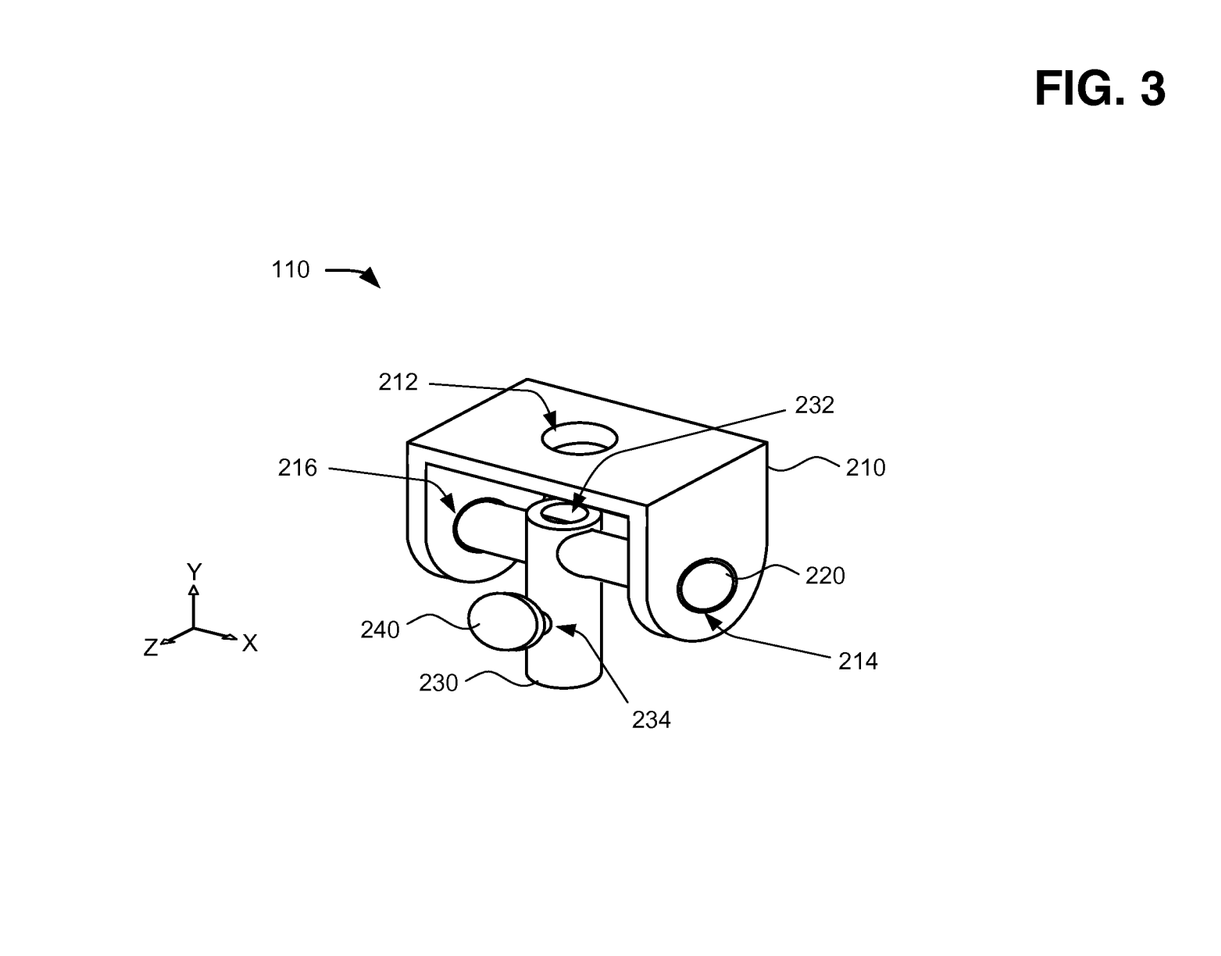
FIG. 3 is an isometric view of an attachment assembly for a cable test platform according to an implementation described herein.
Figure 4A:
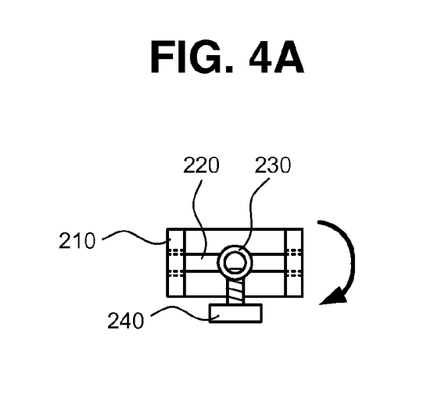
FIG. 4A is a bottom view of the attachment assembly of FIG. 3.
Figure 4B:
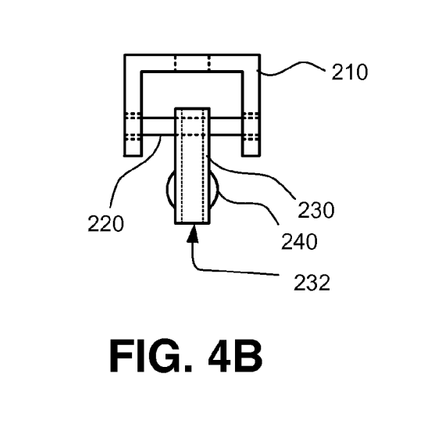
FIG. 4B is a back view of the attachment assembly of FIG. 3.
Figure 4C:
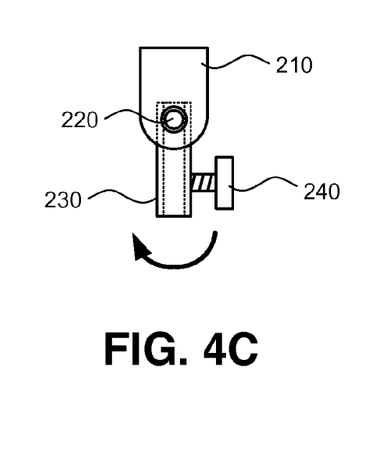
FIG. 4C is a side view of the attachment assembly of FIG. 3.

FIG. 3 is an isometric view of an exemplary attachment assembly 110. FIGS. 4A-4C provide a bottom view, back view, and side view, respectively, of attachment assembly 110. Referring collectively to FIGS. 3-4C, attachment assembly 110 may include a base 210, an axle 220, a securing tube 230, and a set screw 240.

Base 210 may include a top aperture 212 to allow attachment to another surface (e.g., plate 20) of cable test platform 100. In one implementation aperture 212 may be centered on a top portion of base 210, as shown in FIG. 3. Aperture 212 may be configured to receive a fastener (e.g., fastener 120, not shown), such as, a bolt, a pin, a screw, a rotating pin connector, or another attachment mechanism to allow base 210 to be secured to another surface with one degree of rotational freedom (e.g., in a plane parallel to that of plate 20/30). For example, base 210 may be limited to rotation about the Y axis, as shown in FIG. 3. The faster may be secured to plate 20/30. In one implementation, the fastener may include multiple pieces (e.g., bolts, washers, nuts, clips, etc.). In another implementation, the fastener may be configured to enable a user to selectively enable/disable rotation of base 210.

Base 210 may further include two side apertures 214 and 216. Side apertures 214 and 216 may be configured to receive axle 220. For example, in one implementation, one side aperture (e.g., side aperture 214) may include a threaded opening to permit a threaded end of axle 220 to be secured therein. In other implementations, axle 220 may be configured with flanges, pins, or other mechanisms to maintain axle 220 within side apertures 214/216.

Axle 220 may be configured to support securing tube 230 in a manner that limits securing tube 230 to one degree of rotational freedom (e.g., rotating about axle 220). For example, securing tube 230 may be limited to rotation about an X-axis, as shown in FIG. 3. Alternatively, or additionally, axle 220 may rotate within side apertures 214/216 to provide a similar degree of rotational freedom (e.g., about an X-axis of FIG. 3) for securing tube 230.

Securing tube 230 may include an interior bore 232 and a threaded aperture 234. Securing tube 230 and interior bore 232 may be sized to receive an end of cable 10 within a portion interior bore 232. For example, interior bore 232 may have a diameter that is slightly larger than a diameter of cable 10. Threaded aperture 234 may be configured to receive set screw 240. As shown, for example, in FIGS. 3 and 4A, set screw 240 may be inserted through threaded aperture 234 to contact cable 10 within interior bore 232. In other implementations, securing tube 230 may include another type of fastening device (e.g., a clamp, an anchor, a clip, push-in connector, etc.) to secure cable 10 within securing tube 230.

Attachment assembly 110 may be made from various materials, such as, for example, metal (e.g., stainless steel, aluminum, etc.) or a non-metallic material (e.g., plastic, a composite, etc.), depending on the application and/or test strength requirements of attachment assembly 110. In some implementations, some components (e.g., base 210 or securing tube 230) of attachment assembly 110 may be made from different materials than other components (e.g., axle 220 or set screw 240) of attachment assembly 110.

Although FIG. 4 shows exemplary components of attachment assembly 110, in other implementations, attachment assembly 110 may include fewer, different, differently-arranged, or additional components than those depicted in FIG. 4. For example, attachment assembly 110 may include another arrangement that secures cable endpoints to a test platform while allowing two degrees of rotational freedom.

Figure 5:
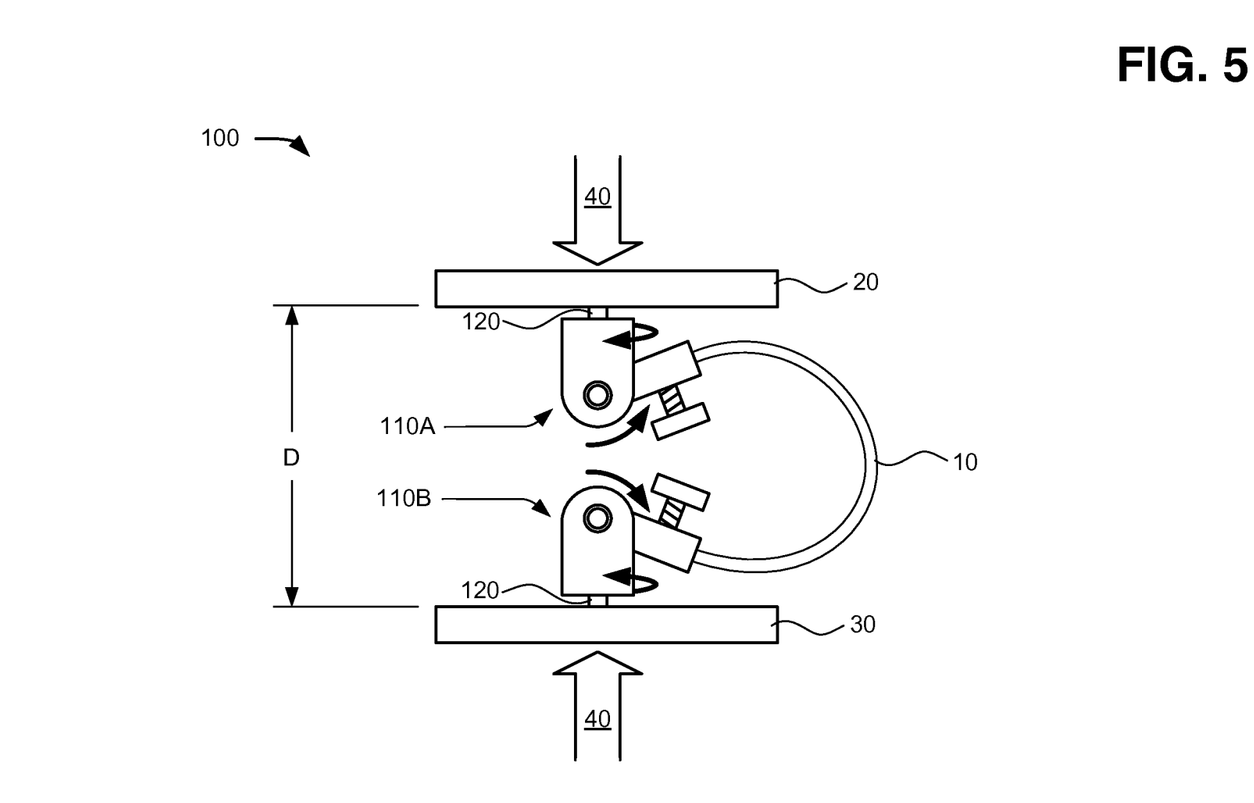
FIG. 5 is a diagram illustrating a compression test according to an implementation described herein.

FIG. 5 is a diagram illustrating a compression test of cable 10 according to an implementation described herein. The compression test arrangement of FIG. 5 may be implemented using cable test platform 100 of FIG. 2 to test bending force of cable 10. As shown in FIG. 5, ends of cable 10 may be secured to plates 20 and 30 via fasteners 120 and attachment assembly 110A or attachment assembly 110B, respectively. Cable 10 may be arranged in a straight run (e.g., with no loops). Compressive force, in the direction shown in FIG. 5, may be applied from force/sensor mechanism 40 via plates 20 and/or 30.

Cable 10 may bend as the force is applied, and the ends of cable 10 may remain secured within attachment assembly 110A and attachment assembly 110B. During bend testing, the compression force applied by plates 20/30 may be measured (e.g., by one or more sensors coupled to plates 20/30). Rotation of attachment assemblies 110 allows for a constant bending cable length to be maintained within cable test platform 100 without causing kinks at the attachment points of cable 10. More particularly, attachment assemblies 110 may rotate about fasteners 120 and about axles 220 as the distance, D, between plates 20 and 30 decreases. Thus, the bending force of the cable may be identified in a test plot (e.g., a graphing of applied force vs. distance between plates 20 and 30) without any discontinuity that would be caused, for example, by separation of cable 10 endpoints from plates 20/30.

Figure 6:
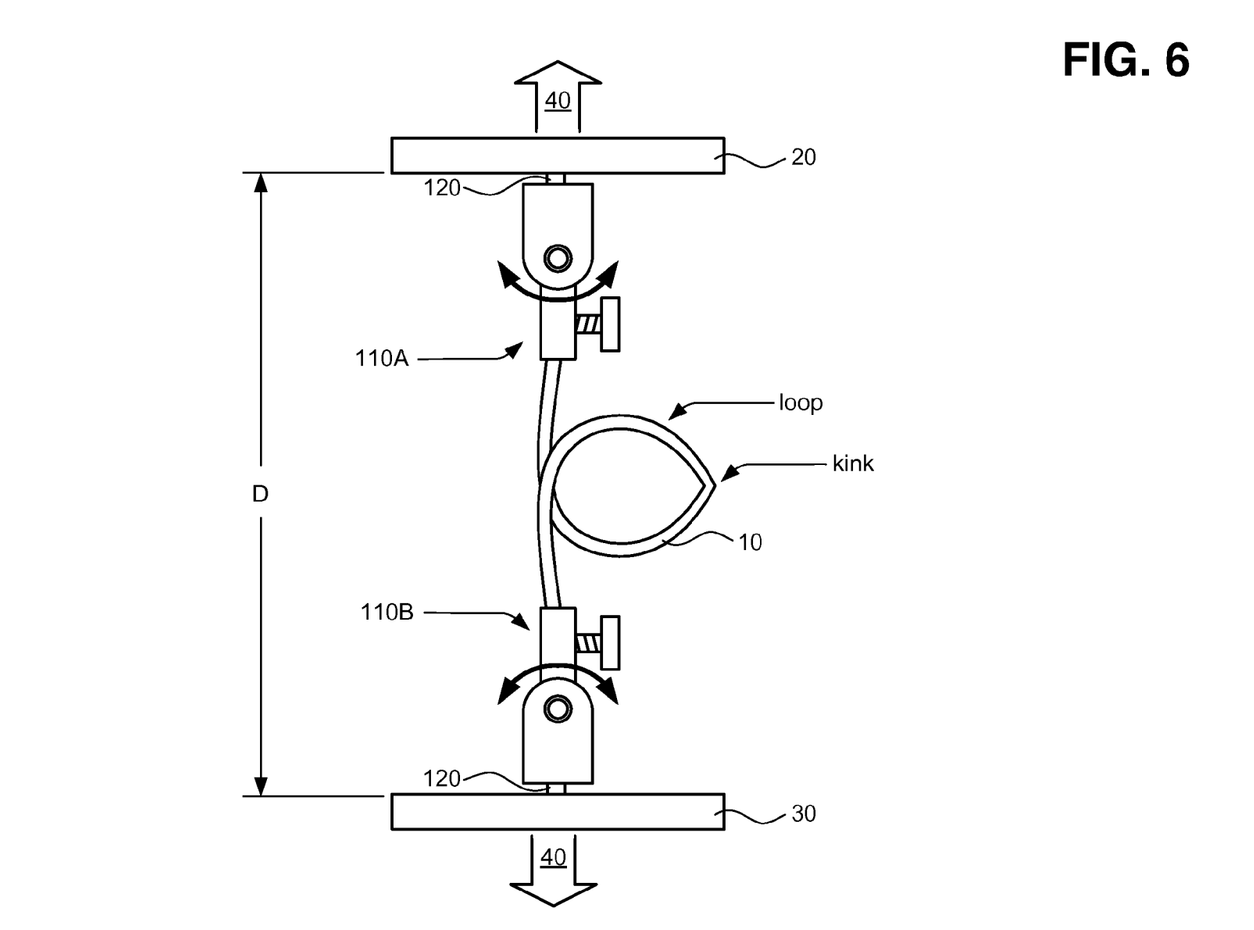
FIG. 6 is a diagram illustrating a pull test according to an implementation described herein.

FIG. 6 is a diagram illustrating a kink test of cable 10 according to an implementation described herein. The kink test arrangement of FIG. 6 may also be implemented using cable test platform 100 of FIG. 2 to test kink force of cable 10. As shown in FIG. 6, ends of cable 10 may be secured to plates 20 and 30 via fasteners 120 and attachment assembly 110A or attachment assembly 110B, respectively. As further shown in FIG. 6, cable 10 may be installed with a loop between endpoints that may be used to cause a kink in cable 10. A linear tensile (or pull) force, in the direction shown in FIG. 6, may be applied by force/sensor mechanism 40 via plates 20 and/or 30.

Cable 10 may bend (e.g., the size of the loop decreases) as the pull force is applied, and the ends of cable 10 may remain secured within attachment assembly 110A and attachment assembly 110B. During kink testing, the pull force applied by plates 20/30 may be measured. When cable 10 kinks (e.g., typically at a point within the loop), the resisting force on the cable is decreased. The kink force may, thus, be identified in a test plot (e.g., a graphing of applied force vs. distance between plates 20 and 30). In one implementation, rotation of attachment assemblies 110 may be limited to movement about axles 220 to prevent the loop in cable 10 from unwinding during testing. More particularly, fasteners 120 may be locked to prevent rotation of attachment assemblies 110 (e.g., in a plane parallel to plates 20/30), while attachment assemblies 110 may still rotate at axles 220 as the distance, D, between plates 20 and 30 increases. In other implementations, two degrees of rotation may be maintained for cable test platform 100.

Figure 7:
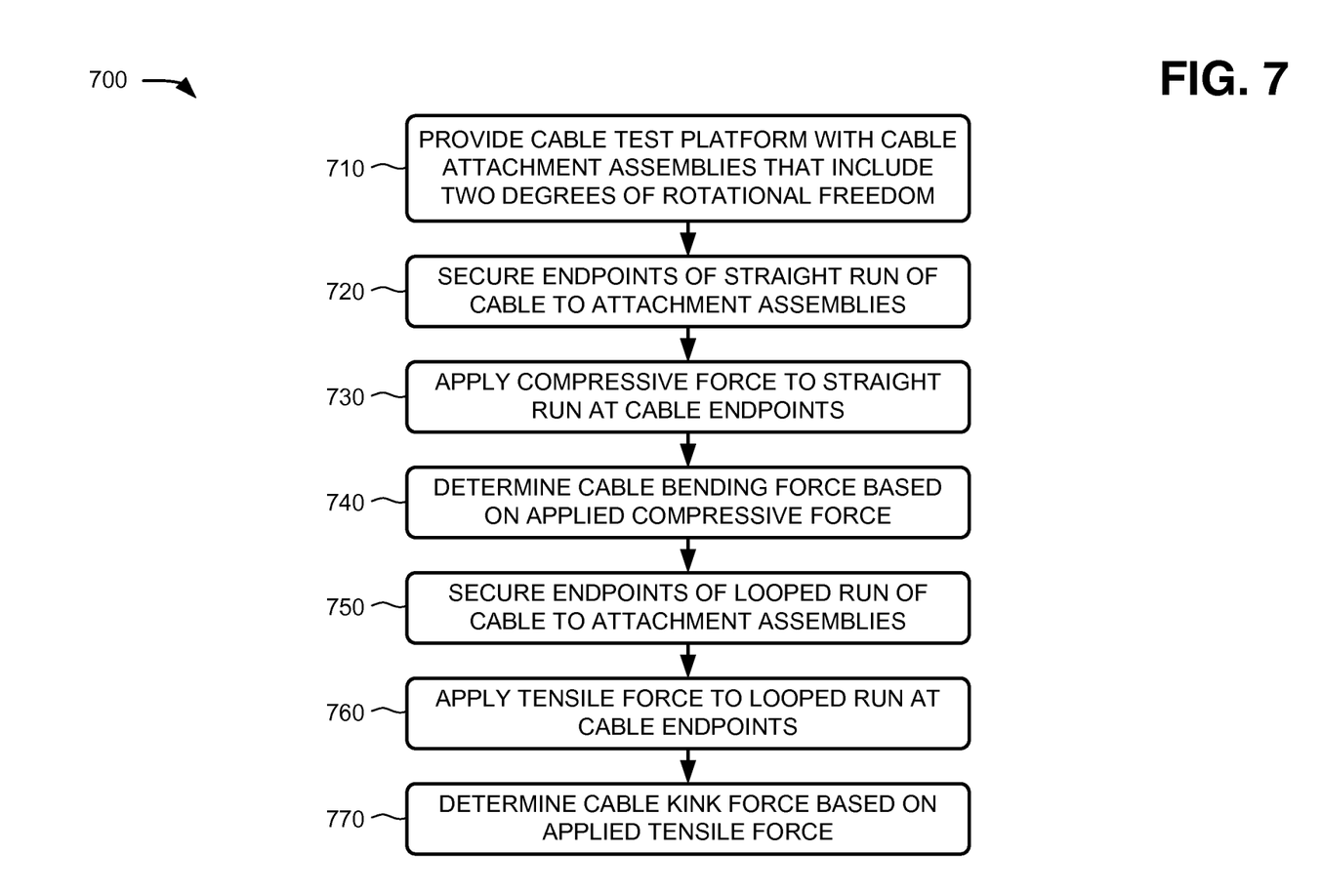
FIG. 7 is a flow chart of a test method for a cable according to an implementation described herein.

FIG. 7 is a flow chart of a process for testing a cable according to an implementation described herein. The test method of FIG. 7 may measure both cable bend force and cable kink force using a single test platform.

Process 700 may include providing a cable test platform with cable attachment assemblies that include two degrees of rotational freedom (block 710). For example, as described above in connection with FIG. 2, cable test platform 100 may be provided that includes plates 20 and 30, force/sensor mechanism 40, and attachment assemblies 110. Plates 20 and 30 may be configured to apply compressive or tensile forces from force/sensor mechanism 40 to cable 10. Attachment assemblies 110 may secure ends of cable 10 to plates 20 and 30. Each of attachment assemblies 110 may provide two degrees of freedom of rotation. The first degree of freedom may be represented as rotation within a plane generally parallel to the plane of plates 20/30. The second degree of freedom may be represented as rotation generally about an axis that is generally parallel to the plane of plates 20/30.

Process 700 may further include securing the endpoints of a straight run of cable to the attachment assemblies (block 720), and applying compressive force to the straight run at the cable endpoints (block 730). For example, as described above in connection with FIG. 5, ends of cable 10 may be secured to plates 20 and 30 via fasteners 120 and attachment assemblies 110. Cable 10 may be arranged in a straight run. Compressive force, in the direction shown in FIG. 5, may be applied by force/sensor mechanism 40 via plates 20 and/or 30.

Process 700 may also include determining a cable bending force based on the applied compressive force (block 740). For example, as described above in connection with FIG. 5, cable 10 may bend as the force is applied, and the ends of cable 10 may remain secured within attachment assemblies 110. During bend testing, the compression force applied by plates 20/30 may be measured. Rotation of attachment assemblies 110 allows for a constant bending cable length to be maintained within cable test platform 100 without causing kinks at the attachment points of cable 10. The bending force of the cable may be identified in a test plot without any discontinuity that would be caused, for example, by separation of cable 10 endpoints from plates 20/30.

Process 700 may further include securing the endpoints of a looped run of cable to the attachment assemblies (block 750), and applying tensile force to the looped run at the cable endpoints (block 760). For example, as described above in connection with FIG. 6, ends of cable 10 may be secured to plates 20 and 30 via fasteners 120 and attachment assemblies 110. Cable 10 may be arranged in a looped run. In one implementation, rotation of attachment assemblies 110 may be limited to allow movement about axles 220 to prevent the loop in cable 10 from unwinding during testing. For example, fasteners 120 may be locked to prevent rotation of attachment assemblies 110 (e.g., in a plane parallel to plates 20/30). Tensile force, in the direction shown in FIG. 6, may be applied to cable 10 by force/sensor mechanism 40 via plates 20 and/or 30.

Process 700 may also include determining a cable kink force based on the applied tensile force (block 770). For example, as described above in connection with FIG. 6, cable 10 may bend (e.g., the size of the loop decreases) as the pull force is applied, and the ends of cable 10 may remain secured within attachment assemblies 110. During the kink testing, the pull force applied by plates 20/30 may be measured. When cable 10 kinks, the resistive force of the cable is decreased. The kink force may, thus, be identified in a test plot.

As described above, systems and/or methods may provide for testing of small diameter cables, such as fiber optic cable, using both compression and pull testing. A cable to be tested may be secured within a set of attachment assemblies that provide two degrees of rotation. The testing may enable measurement of cable bending force (e.g., using compressive forces) and cable kink force (using tensile forces).

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense. For example, while a series of blocks has been described with respect to FIG. 7, the order of the blocks may be modified in other implementations. Further, non-dependent blocks may be performed in parallel.

No element, act, or instruction used in the present application should be construed as critical or essential to the invention unless explicitly described as such. Also, as used herein, the article "a" and "one of" is intended to include one or more items. Further, the phrase "based on" is intended to mean "based, at least in part, on" unless explicitly stated otherwise.

What is claimed is:

1. An apparatus, comprising:
   a first surface configured to apply a linear force in two directions;
   a first attachment assembly configured to secure a first end of a cable to the first surface, wherein the first attachment assembly is further configured to permit two degrees of rotational freedom;
   a second surface, opposite the first surface; and
   a second attachment assembly configured to secure a second end of the cable to the second surface,
   wherein the apparatus facilitates measurement of a bending force and a kink force associated with the cable.

2. The apparatus of claim 1, wherein one of the two degrees of rotational freedom is about an axis that is parallel to the first surface.

3. The apparatus of claim 2, wherein another one of the two degrees of rotational freedom is in a plane parallel to the first surface.

4. The apparatus of claim 1, further comprising a sensor to measure the force applied by the first surface.

5. The apparatus of claim 1, wherein the second surface is configured to apply another linear force in the two directions.

6. The apparatus of claim 1, wherein the second attachment assembly is further configured to permit two degrees of rotational freedom.

7. The apparatus of claim 1, wherein the first attachment assembly is configured to enable a user to selectively disable one of the two degrees of rotational freedom.

8. The apparatus of claim 1, wherein the first attachment assembly includes a base attached to the first surface, and wherein the base is configured to rotate in a plane parallel to the first surface.

9. The apparatus of claim 8, wherein the first attachment assembly further includes an axle that is supported by the base in an orientation parallel to the plane of the first surface and a securing tube that is supported by the axle, and wherein the axle and the securing tube are configured to permit rotation of the first end of the cable about the axle.

10. The apparatus of claim 9, wherein the first attachment assembly further includes a fastening device to hold the first end of the cable within the securing tube.

11. A method, comprising:
   providing a cable test platform with two cable attachment assemblies, wherein at least one of the cable attachment assemblies is configured to provide two degrees of rotational freedom;
   securing ends of the cable to the cable attachment assemblies to form a loop between the ends of the cable;
   applying a tensile force to the cable via the cable attachment assemblies; and
   determining a kink force for the cable based on the applied tensile force.

12. The method of claim 11, further comprising:
   securing ends of another cable to the cable attachment assemblies to form a straight run between the ends of the cable;
   applying a compressive force to the other cable via the cable attachment assemblies; and
   determining a bending force for the other cable based on the applied tensile force.

13. The method of claim 11, wherein both of the cable attachment assemblies are configured to provide two degrees of rotational freedom.

14. The method of claim 11, wherein one of the two degrees of rotational freedom is about an axis that is an orthogonal plane to a direction of the applied tensile force.

15. The method of claim 14, wherein another one of the two degrees of rotational freedom is about an axis that is parallel to the direction of the applied tensile force.

16. The method of claim 14, further comprising:
   disabling the other one of the two degrees of rotational freedom before applying the tensile force.

17. An attachment assembly for a cable testing platform including two surfaces that apply linear force to a cable therein, comprising:
   a base attached to a first surface of the two surfaces, wherein the base is configured to rotate in a plane orthogonal to the direction of the applied linear force;
   an axle, supported by the base in the plane orthogonal to the direction of the applied linear force; and
   a securing tube configured to receive an end of the cable, wherein the securing tube is supported by the axle and further configured to permit rotation of the securing tube about the axle.

18. The attachment assembly of claim 17, further comprising:
   a fastening device to secure the end of the cable within the securing tube.

19. The attachment assembly of claim 17, further comprising:
   a fastener configured to secure the base to the first surface, wherein the fastener is configured to enable selective enabling and disabling of rotation of the base.

20. The attachment assembly of claim 17, wherein the attachment assembly secures the end of the cable against both tensile force and compressive force.

* * * * *